US008744046B2

(12) United States Patent
Yamauchi et al.

(10) Patent No.: US 8,744,046 B2
(45) Date of Patent: Jun. 3, 2014

(54) METHOD AND APPARATUS OF PRECISELY MEASURING INTENSITY PROFILE OF X-RAY NANOBEAM

(75) Inventors: Kazuto Yamauchi, Suita (JP); Hidekazu Mimura, Suita (JP); Hiromi Okada, Kobe (JP)

(73) Assignees: JTEC Corporation, Kobe-shi (JP); Osaka University, Suita-shi (JP)

( * ) Notice: Subject to any disclaimer, the term of this patent is extended or adjusted under 35 U.S.C. 154(b) by 315 days.

(21) Appl. No.: 13/203,095

(22) PCT Filed: Mar. 19, 2009

(86) PCT No.: PCT/JP2009/055474
§ 371 (c)(1), (2), (4) Date: Aug. 24, 2011

(87) PCT Pub. No.: WO2010/097968
PCT Pub. Date: Sep. 2, 2010

(65) Prior Publication Data

US 2011/0305317 A1 Dec. 15, 2011

(30) Foreign Application Priority Data

Feb. 27, 2009 (JP) ................................ 2009-045688

(51) Int. Cl.
*G01N 23/20* (2006.01)

(52) U.S. Cl.
USPC ............................................. 378/70; 378/71

(58) Field of Classification Search
USPC ............................................. 378/70, 71, 207
See application file for complete search history.

(56) References Cited

FOREIGN PATENT DOCUMENTS

| | | |
|---|---|---|
| JP | 10-319196 | 12/1998 |
| JP | 2008-164553 A1 | 7/2008 |

OTHER PUBLICATIONS

H. Mimura, et al.; "Direct determination of the wave field of an x-ray nanobeam;" Physical Review A; vol. 77; 2008; pp. 015812-1-015812-4 and 2 end sheets (6 sheets total)/Cited in International Search Report.

International Search Report for International Application No. PCT/JP2009/055474 dated Apr. 8, 2009.

*Primary Examiner* — Courtney Thomas
(74) *Attorney, Agent, or Firm* — Kratz, Quintos & Hanson, LLP

(57) ABSTRACT

Provided are a method and an apparatus of precisely measuring the intensity profile of an x-ray nanobeam, which can measure x-rays having different wavelengths with one knife edge and can perform optimal measurements corresponding to the depth of focus of an x-ray beam and the conditions of other measurement devices, using a dark field measurement method which enables precise measurements of the profile of an x-ray beam using a knife edge and using diffracted and transmitted x-rays. The knife edge (4) is formed of a heavy metal which advances the phase of an x-ray passing therethrough and is fabricated in such a manner that the thickness may change in the longitudinal direction continuously or in a stepwise fashion. The knife edge (4) is so set that an x-ray beam may traverse the knife edge (4) at such a thickness position as to achieve a phase shift in a range wherein a transmitted x-ray and a diffracted x-ray diffracted at the end of the knife edge may reinforce each other, and a superposed x-ray of the diffracted x-ray and the transmitted x-ray is measured by an x-ray detector.

9 Claims, 12 Drawing Sheets

1 2 8 5 6 3 7 4

(a)

(b)

(a)

(b)

(a)

(b)

(a)

(b)

METHOD AND APPARATUS OF PRECISELY MEASURING INTENSITY PROFILE OF X-RAY NANOBEAM

TECHNICAL FIELD

The present invention relates to a method and apparatus for precision measurement of an X-ray nanobeam intensity distribution, and more specifically, to a method and apparatus for precision measurement of an X-ray nanobeam intensity distribution that make it possible to measure an intensity distribution of X-ray nanobeams in soft X-ray to hard X-ray regions, with nm-order spatial resolutions.

BACKGROUND ART

High-brightness, low-emittance, and high-coherence X-rays in various wavelength regions from soft X-rays to hard X-rays have become available at third-generation synchrotron radiation facilities represented by SPring-8. This has dramatically improved analytical sensitivities and spatial resolutions at various analyses such as fluorescent X-ray analysis, photoelectron spectrometry, and X-ray diffraction. These X-ray analyses and X-ray microscopic approaches using radiation light not only provide high sensitivities and high resolutions but also allow nondestructive observations, and thus are currently being employed in the fields of medicine, biology, and material science, and the like.

Highly collected X-ray nanobeams are required to utilize various X-ray analytical technologies with high spatial resolutions at synchrotron radiation facilities. A group of the inventors has already succeeded in collecting an X-ray with a wavelength of 0.6 Å in a spot diameter of 100 nm or less, by using a light collection optical system including a Kirkpatrick and Baez (K-B) mirror. This success is largely due to a uniquely developed high-precision mirror processing technique and high-precision mirror shape measurement techniques. This processing technique refers to numerically-controlled elastic emission machining (EEM) which is performed on a process principle: a high shear flow of ultrapure water mixed with fine particles is formed along a surface of a mirror to be processed; the fine particles combine together with atoms on the surface of the mirror by a kind of chemical reaction; and the surface atoms are removed with movement of the fine particles. In addition, the shape measurement technologies refer to microstitching interferometry (MSI) and relative angle determinable stitching interferometry (RADSI) which are performed on a measurement principle that pieces of partial shape data from an interferometer capable of high-precision shape measurement of small areas are put together to obtain the entire shape data. Using the shape measurement techniques makes it possible to measure accurately the shape of an X-ray mirror in all space wavelength ranges with a measurement reproducibility of 1 nm or less of PV value. The group has successfully prepared an X-ray light collecting mirror with an accuracy of 2 nm (PV value) using these techniques, thereby to realize diffraction-limited light collection of SPring-8 hard X-rays at a level of sub-30 nm.

The inventors aim to realize sub-10 nm light collection for implementation of the world's best ultrahigh-resolution scanning X-ray microscope and ultrahigh-resolution X-ray micro CT. To that end, extremely strict shape accuracy is required for X-ray mirrors as follows: a shape error is P-V1 nm or less in mid- and long-term space wavelengths; a designed mirror shape has a deep curve; a multilayer film is essentially formed on a mirror surface to provide a deep X-ray incident angle, and the like. Accordingly, it is extremely difficult to determine a phase error in a surface of an X-ray mirror with respect to an ideal surface by off-line measurement using an interferometer or the like. The inventors therefore have proposed an at-wavelength metrology in which a phase error in a mirror surface is determined by phase retrieval calculation only from X-ray intensity profile information in a light collection plane, and proposed an X-ray collection method in which a phase error of a light collection optical system is corrected using the foregoing metrology to eliminate irregularities in a wavefront of a focal plane (JP 2006-357566 (JP 2008-164553 A)). To calculate precisely a phase error of an X-ray mirror by the phase retrieval method, it is essentially required to acquire an accurate X-ray collection intensity profile.

Conventionally, an X-ray beam intensity profile is measured in such a manner as to cut off an X-ray beam little by little by a knife edge or a wire while measuring changes in light intensity as described in Patent Document 1. FIG. 14 shows a measurement optical system using a wire scanning method. In this optical system, an incident X-ray 100 is passed through a slit 101 so as to be limited to a predetermined width, then is passed through an ion chamber 102, and then is reflected and collected by a surface of an X-ray mirror 103. In the foregoing arrangement, an Au wire 104 with a diameter of 200 μm sufficiently larger than a diameter of an X-ray beam is run by a piezo stage in a light collection plane vertically to the mirror surface, thereby to gradually cut off a collected beam while measuring changes in X-ray intensity behind the focal point through the slit 105 by an X-ray detector 106. In this arrangement, as the X-ray detector 106, an avalanche photodiode (APD) with high sensitivity and fast output responsibility is used. The X-ray intensities measured by the X-ray detector 106 are standardized in accordance with an incident X-ray intensity measured at the ion chamber 102. The slit 105 is provided to eliminate influence of inclination of the wire 104 with respect to the beam on measurement of a light collection intensity profile. FIG. 15(*a*) shows changes in X-ray intensity profile measured by the X-ray detector 106. These changes are differentiated with respect to wire positions, thereby to obtain a light collection intensity profile as shown in FIG. 15(*b*).

However, the wire scanning method has two problems: it is difficult to prepare a geometrically sharp knife edge with a sufficient thickness so as not to let an X-ray pass through; and noise generated at intensity measurement is enhanced at the time of differentiation. In addition, although accurate information is needed in a wide base region of an X-ray intensity profile to calculate precisely a phase error of an X-ray mirror by phase retrieval, the conventional wire scanning method provides information in this region with low reliability.

Accordingly, in order to provide a method and apparatus for precise measurement of an X-ray nanobeam intensity distribution that overcome the problem of noise enhancement due to background noise and differentiation associated with the wire scanning method and realize higher-precision X-ray beam profile measurement, the inventors propose a method for precise measurement of an X-ray nanobeam intensity distribution that use a dark-field metrology to run a knife edge so as to cut across an X-ray beam and measure an X-ray intensity by an X-ray detector disposed behind the knife edge at a position geometrically dark with respect to an X-ray source, thereby to measure an X-ray intensity distribution in a cross section of the X-ray beam, wherein the knife edge is made of a heavy metal with the effect of advancing a phase of an X-ray passing through the knife edge, a thickness of the knife edge is set so as to obtain a phase shift to an extent that the transmission X-ray and a diffraction X-ray diffracted by a leading end of the knife edge reinforce each other, and an X-ray formed by overlapping of the diffraction X-ray and the transmission X-ray is measured by the X-ray detector.

Patent Document 1: JP-A No. 10-319196

SUMMARY OF INVENTION

Technical Problem

In the foregoing measurement method proposed by the inventors, however, a knife edge of a theoretically optimum thickness is used for an X-ray of a specific wavelength, which means that knife edges of different thicknesses are needed for X-rays of different wavelengths. This causes troublesome replacement tasks of knife edges and requires uneconomically a large number of expensive knife edges. In addition, setting the thickness of a knife edge at a theoretically optimum value may not realize optimum intensity measurement, depending on a focal depth of an X-ray beam and other conditions of the measurement apparatus.

In light of the foregoing circumstances, an object of the present invention is to provide a method and apparatus for precise measurement of an X-ray nanobeam intensity distribution that use a dark-field metrology allowing high-precision measurement of an X-ray beam profile using a knife edge, a diffraction X-ray, and a transmission X-ray, support measurement of X-rays of different wavelengths with one knife edge, and realize optimum measurement in accordance with a focal depth of an X-ray beam and other conditions of the measurement apparatus.

Solution to Problem

To solve the foregoing problem, the present invention provides a method for precise measurement of an X-ray nanobeam intensity distribution that uses a dark-field metrology to run a knife edge so as to cut across an X-ray beam and measure an X-ray intensity by an X-ray detector disposed behind the knife edge at a position geometrically dark with respect to an X-ray source, thereby to measure an X-ray intensity distribution in a cross section of the X-ray beam, wherein the knife edge is made of a heavy metal with the effect of advancing a phase of an X-ray passing through the knife edge, prepared so as to change in thickness continuously or stepwise in a longitudinal direction, and set so as to cut across an X-ray beam at a position of a thickness as to obtain a phase shift with which a transmission X-ray and a diffraction X-ray diffracted by a leading end of the knife edge reinforce each other, and an X-ray formed by overlapping of the diffraction X-ray and the transmission X-ray is measured by the X-ray detector (Claim 1).

In addition, preferably, the knife edge is formed so as to change in thickness from 1 to 5 μm continuously or stepwise in a longitudinal direction and is set so as to cut across an X-ray beam at a position of a thickness where a transmission rate of an X-ray passing through the knife edge falls within a range from 80 to 20% and a phase shift becomes 0.3 to 0.7λ (λ denotes wavelength of an X-ray), and an X-ray formed by overlapping of a diffraction X-ray that has been diffracted at a leading end of the knife edge and come around behind the knife edge and a transmission X-ray that has been passed through the knife edge and advanced in phase, is measured by the X-ray detector (Claim 2).

In this arrangement, the material for the knife edge is preferably Pt or Au (Claim 3). More preferably, a leading end portion of the knife edge is rectangular in cross section, and a leading end surface of the knife edge has an inclination angle of 1 mrad or less (Claim 4); or the leading end portion of the knife edge is rectangular in cross section, and an angle formed by the leading end surface of the knife edge and an optical axis of an X-ray beam is set at 1 mrad or less (Claim 5).

Further preferably, an edge member with the knife edge is run in a direction that the knife edge cuts across an X-ray beam and in a direction along a longer side of the knife edge (Claim 6).

In addition, for solving the foregoing problem, the present invention provides an apparatus for precise measurement of an X-ray nanobeam intensity distribution, comprising: an edge member that varies in thickness continuously or stepwise in a longitudinal direction and includes a knife edge with a leading end portion rectangular in cross section and disposed such that an inclination angle of a leading end surface becomes 1 mrad or less with respect to an optical axis of an X-ray beam; a high-accurate moving stage that holds the edge member such that the knife edge is run in a direction that cuts across the X-ray beam and in a direction along a longer side of the knife edge; and an X-ray detector that is disposed behind the knife edge at a position geometrically dark with respect to an X-ray source, wherein the knife edge is made of a heavy metal with the effect of advancing a phase of an X-ray passing through the knife edge and is set so as to cut across an X-ray beam at a position of a thickness as to obtain a phase shift with which a transmission X-ray and a diffraction X-ray diffracted by a leading end of the knife edge reinforce each other, and an X-ray formed by overlapping of the diffraction X-ray and the transmission X-ray is measured by the X-ray detector (Claim 7).

Further, preferably, the knife edge is formed so as to change in thickness from 1 to 5 μm continuously or stepwise in a longitudinal direction, and is set so as to cut across an X-ray beam at a position of a thickness where a transmission rate of an X-ray passing through the knife edge falls within a range from 80 to 20% and a phase shift becomes 0.3 to 0.7λ (λ denotes wavelength of an X-ray), and an X-ray formed by overlapping of a diffraction X-ray that has been diffracted at a leading end of the knife edge and come around behind the knife edge and a transmission X-ray that has been passed through the knife edge and advanced in phase, is measured by the X-ray detector (Claim 8).

More preferably, a slit is arranged in front of the X-ray detector such that an opening thereof is situated at a position geometrically dark with respect to an X-ray source (Claim 9).

Advantageous Effects of Invention

According to a method and apparatus for precise measurement of an X-ray nanobeam intensity distribution in the present invention, a diffraction X-ray intensity can be directly detected in proportion to an X-ray intensity at the leading end position of a knife edge in a geometrically dark section, which eliminates the need for differential processing required in the conventional wire scanning method and thus allows measurement with low background noise. In addition, the knife edge is made of a heavy metal with the effect of advancing a phase of an X-ray passing through the knife edge, a thickness of the knife edge is set so as to obtain a phase shift with which a transmission X-ray and a diffraction X-ray diffracted at the leading end of the knife edge reinforce each other, and an X-ray formed by overlapping of the diffraction X-ray and the transmission X-ray is measured by an X-ray detector. This enhances a signal level, which increases an S/N ratio allowing measurement of an X-ray intensity distribution with high sensitivity and high spatial resolution. In particular, it is possible to measure an intensity distribution of an X-ray nanobeam collected with a full width at half maximum of a beam waist of 100 nm or less, with nm-order spatial resolutions.

In addition, the thickness of the knife edge is changed continuously or stepwise with respect to the optical axis of an X-ray, and the edge member with the knife edge is run in a direction that changes in thickness and is orthogonal to the direction of the optical axis, thereby allowing the knife edge to be optimum in thickness with respect to the wavelength of an X-ray. If a focal depth of an X-ray is shallow, although sensitivity is sacrificed, a thinner portion of the knife edge can be used to obtain a sharp profile. Further, if the wavelength of an X-ray is unknown, it is possible to obtain a wavelength range of the unknown X-ray by deriving the thickness of the knife edge with a maximum diffraction X-ray intensity with respect to the X-ray of an unknown wavelength, or deriving thickness-intensity measurement characteristics from measurement of changes in diffraction X-ray intensity with respect to changes in thickness of the knife edge, and determining the wavelength range by back calculation from comparison between the thickness-intensity measurement characteristics and thickness-intensity calculation characteristics obtained by calculating the diffraction X-ray intensity with respect to the wavelength of the X-ray and the thickness of the knife edge.

BRIEF DESCRIPTION OF THE DRAWINGS

FIG. 6(*a*) illustrates a base cut away from an Si wafer; FIG. 6(*b*) illustrates the base on which Pt is evaporated; and FIG. 6(*c*) illustrates formation of the knife edge with a predetermined thickness by carving out of a periphery of the base by an FIB processing device;

FIG. 11(*a*) is a perpendicular view of an outer appearance of the edge member; and FIG. 11(*b*) is a plane view of the edge member;

FIG. 12(*a*) is a partial plane view of a knife edge of a two-sided inclination type which has on both sides inclination planes symmetric with respect to a center line and changes in thickness in a continuous manner; FIG. 12(*b*) is a partial plane view of a knife edge of a single-sided inclination type which has an inclination plane on one side and an orthogonal plane on the other side, and changes in thickness in a continuous manner; FIG. 12(*c*) is a partial plane view of a knife edge of a two-sided stepped type which has on both sides stepped planes symmetric with respect to a center line, and changes in thickness in a stepwise manner; and FIG. 12(*d*) is a partial plane view of a knife edge of a single-sided stepped type which has a stepped plane on one side and an orthogonal plane on the other side, and changes in thickness in a stepwise manner;

FIG. 15(*a*) is a graph showing changes in X-ray intensity with displacement of a wire; and FIG. 15(*b*) is a graph showing an X-ray intensity profile obtained by differentiating the results (a).

DESCRIPTION OF EMBODIMENTS

Figure 1:
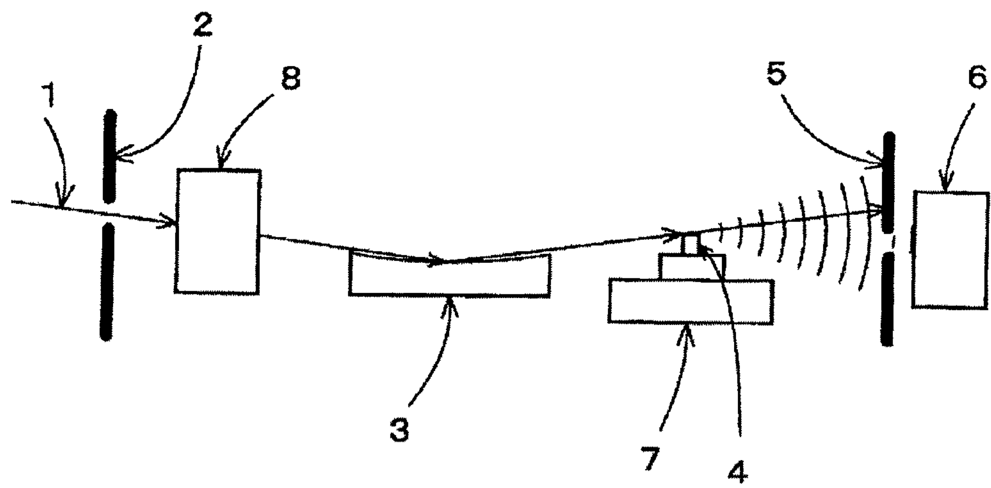
FIG. 1 is a general arrangement diagram of a measurement optical system for realizing a method for precise measurement of an X-ray nanobeam intensity distribution in the present invention.
Figure 2:
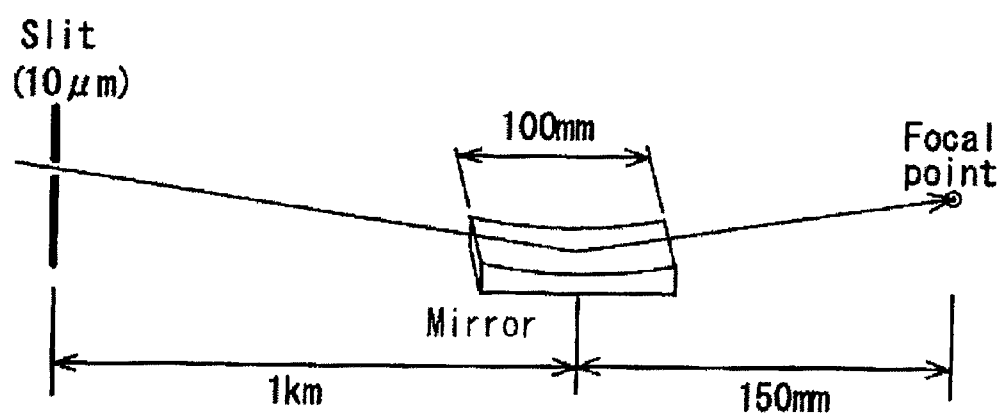
FIG. 2 is an illustrative diagram showing a sub-30 nm light collection optical system used for measurement of an X-ray beam intensity distribution.

The present invention will be described in more detail with reference to the attached drawings. FIG. 1 is a general arrangement diagram of a measurement optical system using a method for precise measurement of an X-ray nanobeam intensity distribution, and FIG. 2 shows an X-ray beam collection optical system used for measurement.

In this embodiment, as shown in FIG. 1, an incident X-ray 1 passes through a slit 2 and obliquely enters into an X-ray mirror 3 having an oval form where the incident X-ray 1 is subjected to one-dimensional light collection. In addition, a knife edge 4 is disposed on an X-ray beam focal plane and a slit 5 is arranged behind the knife edge 4 to shut off a direct X-ray beam, and an X-ray intensity is measured by an X-ray detector 6 that is disposed behind the knife edge 4 at a position geometrically dark with respect to an X-ray source. The knife edge 4 is held by a moving stage 7, and the moving stage 7 is driven to run the knife edge 4 so as to cut across the X-ray beam. In this embodiment, the moving stage 7 is configured as a piezo-stage to provide a running accuracy of 1 nm. In addition, the moving stage 7 is configured to move the knife edge 4 in a direction of an optical axis of an X-ray beam and adjust an angle of inclination of the knife edge 4 with respect to an X-ray beam.

In this arrangement, the X-ray detector 6 uses an avalanche photodiode (APD) with high sensitivity and fast output responsibility. In addition, for standardization of an X-ray intensity measured by the X-ray detector 6, an ion chamber 8 is disposed immediately in front of the X-ray mirror 3 to thereby measure an incident X-ray intensity at any time.

Figure 3:
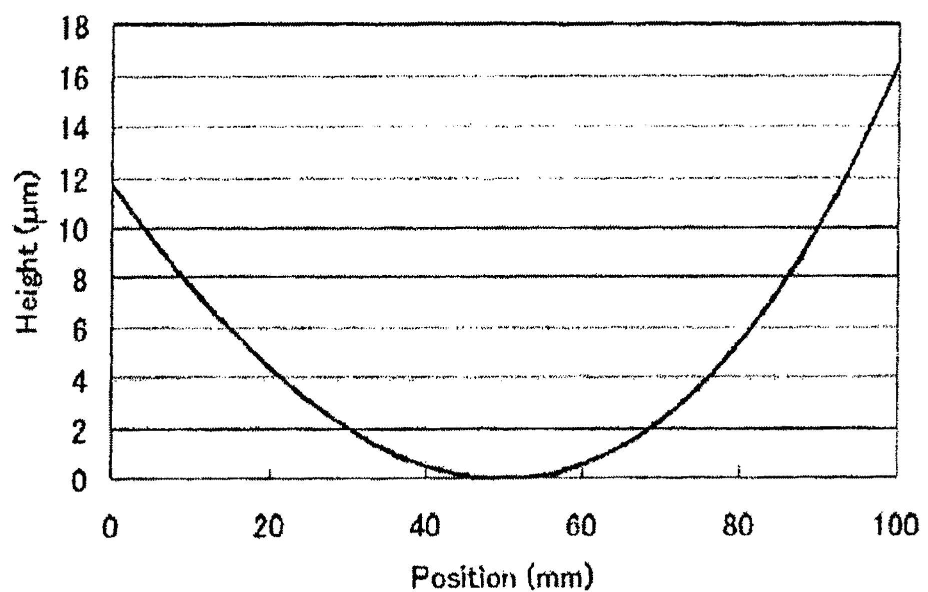
FIG. 3(*a*) is a graph showing a designed mirror shape of the sub-30 nm light collection optical system, and FIG. 3(*b*) is a graph showing an ideal light collection profile.
Figure 3:
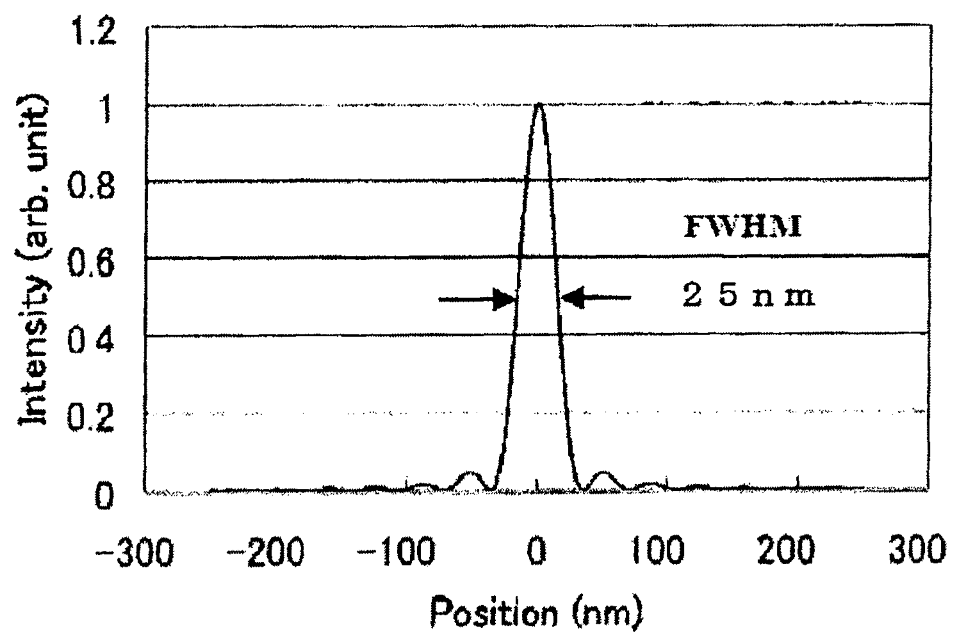

The X-ray beam used in this embodiment is a SPring-8 1 km-long beam line (BL29XUL) with X-ray energy of 15 keV (wavelength $\lambda$=0.8 Å). FIGS. 2 and 3 show characteristics of an X-ray beam collection optical system. As shown in FIG. 2, the X-ray beam passes through a 10 μm-wide slit, and then is collected by an X-ray mirror 1 km ahead, at a position at a focal distance of 150 mm. As shown in FIG. 3(*a*), the X-ray mirror has a reflection plane designed to have an oval shape 100 mm long and about 10 μm deep in a central portion. In addition, the reflection plane of the X-ray mirror has a shape accuracy of 2 nm (PV value) or less. FIG. 3(*b*) shows an ideal light collection profile with the thus designed X-ray mirror. If light collection is performed by an ideal X-ray mirror, a full width at half maximum (FWHM) of a beam waist is about 25 nm. The oval X-ray collection mirror utilizes geometrical nature of an oval to preserve a wavefront by maintaining at a constant level an X-ray overall optical path length from a light source to a focal point, and obtain ideal light collection with complete phase matching at the focal point.

A method for precise measurement of an X-ray nanobeam intensity distribution in the present invention uses a dark-field metrology to run a knife edge so as to cut across an X-ray beam and measure an X-ray intensity by an X-ray detector disposed behind the knife edge at a position geometrically dark with respect to an X-ray source, thereby to measure an X-ray intensity distribution in a cross section of the X-ray beam, and the method is characterized in that the knife edge is made of a heavy metal with the effect of advancing a phase of an X-ray passing through the knife edge, a thickness of the knife edge is set so as to obtain a phase shift to an extent that the transmission X-ray and a diffraction X-ray diffracted by a leading end of the knife edge reinforce each other, and an X-ray formed by overlapping of the diffraction X-ray and the transmission X-ray is measured by the X-ray detector.

Measurement principle of the present invention will be briefly described below. When a leading edge portion of the knife edge is positioned in an X-ray beam formed by a planar wave, a phenomenon (diffraction) occurs that a spherical wave is generated at the edge portion and the X-ray comes around behind the knife edge. In addition, part of the X-ray passes through the leading edge portion of the knife edge. If the material for the knife edge has the effect of advancing a phase of the X-ray passing through the knife edge, the phase of the transmission X-ray shifts depending on the thickness of the knife edge and the transmission X-ray decreases in intensity. Then, the diffraction X-ray and the transmission X-ray overlap behind the leading edge portion of the knife edge. If the phase shift of the transmission X-ray occurs only by a half-wavelength with a sufficient transmission intensity maintained, the transmission X-ray and the diffraction X-ray reinforce each other at the time of overlapping. The inventors have discovered from results of simulations that an X-ray having reached behind the knife edge has an intensity in proportion to the X-ray beam intensity at the edge portion. Accordingly, measuring the intensity of this X-ray at a position geometrically dark with respect to the X-ray beam, allows direct measurement of an intensity profile of the X-ray beam without influence of background noise. In addition, without the need to differentiate measured values as in the conventional wire scanning method, the measurement method of the present invention makes it possible to avoid enhancement of noise and minimize influence of noise, thereby to realize high-sensitivity, high-precision measurement.

In addition, the X-ray detector is disposed at a position that does not detect directly the transmission X-ray having passed through the knife edge 4. Alternatively, the slit 5 disposed in front of the X-ray detector 6 shut off the X-ray. In addition, the X-ray detector 6 is arranged at a position distant as much as possible from a geometrical light path of the X-ray beam for detection of intensities of the diffraction X-ray and the transmission X-ray. In this arrangement, positional accuracies required for the X-ray detector 6 and the slit 5 are lower because the diffraction X-ray does not greatly change in intensity even if the position of the X-ray detector 6 is displaced by 3 to 5 mm. Regarding this point, the inventors have verified from simulations that positional dependence of the diffraction X-ray intensity on the X-ray detector 6 is extremely low in a geometrically dark section.

In this arrangement, a typical heavy metal with the effect of advancing a phase of a transmission X-ray is Pt or Au. Alternatively, other heavy metals may be used for an optimum designed thickness in accordance with a wavelength and a focal depth of an X-ray and a required spatial resolution. Although the X-ray beam handled in this embodiment has energy of 10 to 20 keV (with a wavelength of 1.2 to 0.6 Å), it is also possible to measure an intensity distribution of X-ray beams in a wider range of wavelengths. Since an X-ray of a longer wavelength has a larger amount of phase shift, measurement with higher spatial resolution is allowed using a thinner knife edge. Further, there is a possibility that the technique of the present invention can be employed to measure an intensity distribution of an extreme ultraviolet ray of a wavelength of 13.5 nm used for extreme ultra violet lithography (EUVL) as a next-generation semiconductor exposure technology.

Figure 4:
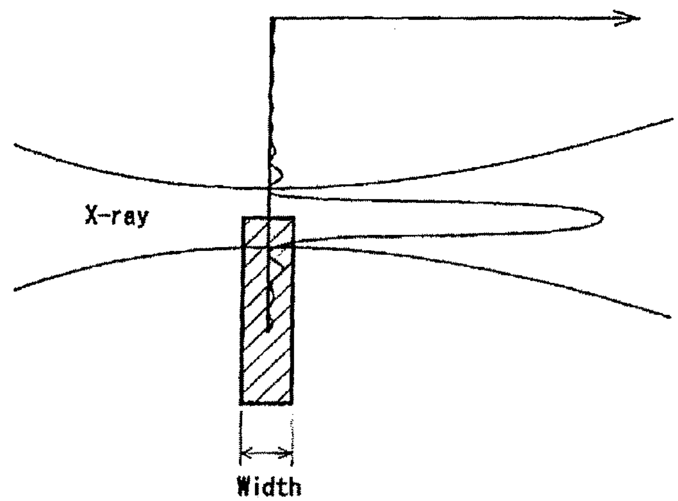
FIG. 4(*a*) is an arrangement diagram showing a relationship between a knife edge and an X-ray beam, and FIG. 4(*b*) is a graph showing relationships among an intensity of a transmission X-ray, a phase shift of the transmission X-ray, and an intensity of a diffraction X-ray, with changes in thickness of the knife edge.
Figure 4:
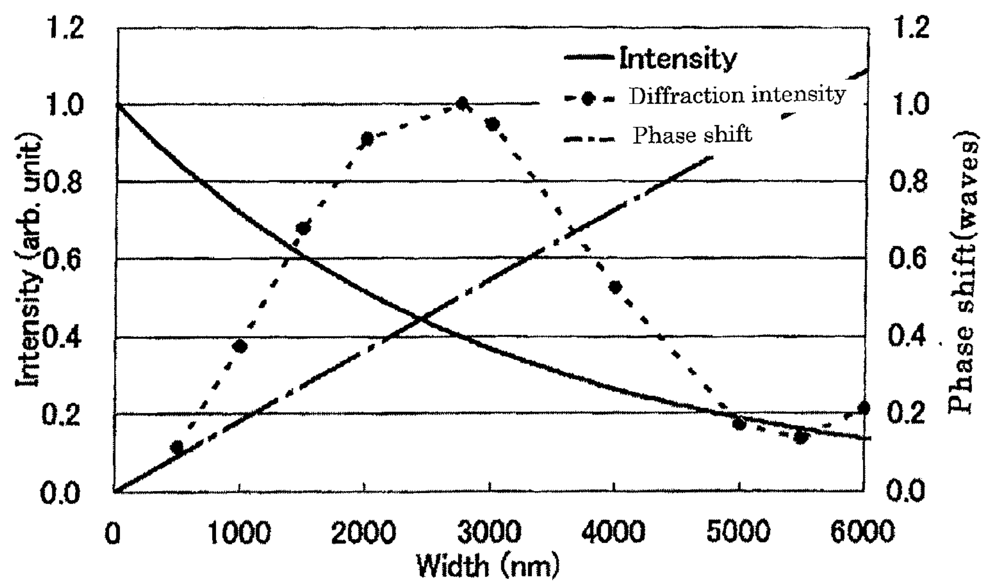

Next, the inventors have performed simulations using Pt as the material for the knife edge, and estimated an optimum thickness of the knife edge for measurement of a light collection intensity profile of an X-ray with a wavelength of 0.8 Å collected by an oblique incident optical system, and a shape accuracy of the leading edge portion of the knife edge. The estimated results will be described with reference to FIGS. 4 and 5. As shown in FIG. 4(*a*), the knife edge is placed with the thickness oriented in the direction of the optical axis and with the edge portion positioned in a center of an X-ray beam. In this state, as shown in FIG. 4(*b*), an intensity of a transmission X-ray (solid line), a phase shift of the transmission X-ray (chain line), an intensity of a diffraction X-ray (dotted line) were calculated with changes in thickness of the knife edge. With increase in thickness of the knife edge, the phase shift of the transmission X-ray increases linearly but the intensity of the transmission X-ray decreases exponentially. Therefore, the intensity of the diffraction X-ray does not always become highest when the phase shift of the transmission X-ray takes places by a half wavelength. Practically, the thickness of the knife edge may be set such that the intensity of the diffraction X-ray falls within a range covering about 80% of the maximum value. Nevertheless, the knife edge is preferably thinner as much as possible within an allowable range because the thinner knife edge provides a higher spatial resolution. From the foregoing results, in this embodiment, the Pt knife edge with a thickness of 2,000 nm (2 μm) is used for an X-ray beam with a wavelength of 0.8 Å.

Figure 5:
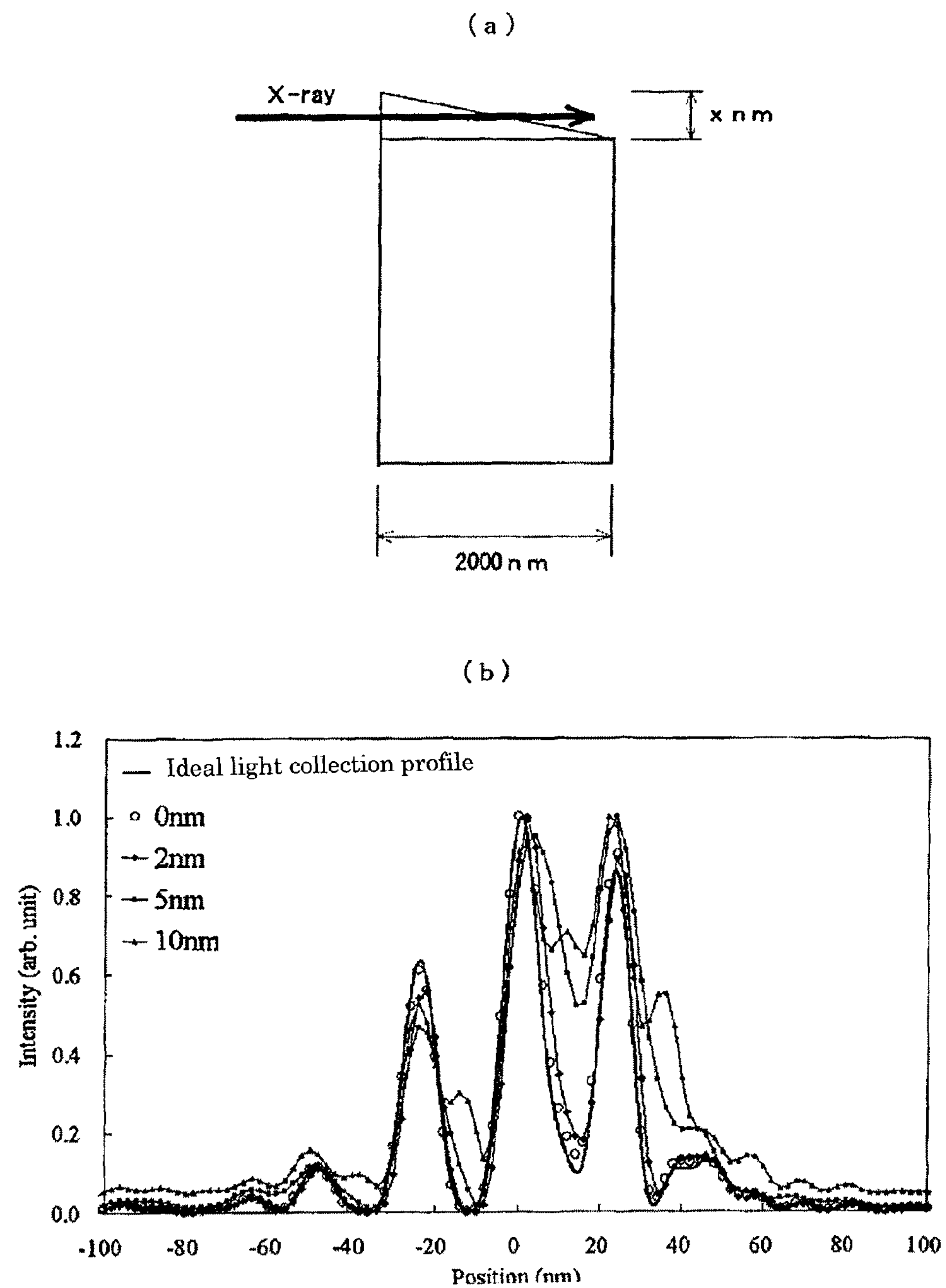
FIG. 5(*a*) is an illustrative diagram showing a positional relationship between a leading end shape of the knife edge and an X-ray beam, and FIG. 5(*b*) is a graph showing calculation results of a light collection profile with changes in inclination of the leading end of the knife edge.

In addition, the inventors have estimated a required shape accuracy of the leading edge portion of the knife edge by calculating an intensity profile with variations in x on the basis of a model shown in FIG. 5(*a*). Specifically, the inventors have added a right-triangular portion to a leading end surface of a 2,000-nm thick knife edge rectangular in cross section, and calculated an intensity of a diffraction X-ray on the knife edge while changing an inclination angle of the leading end surface with variations in x of 0 nm, 2 nm, 5 nm, and 10 nm as shown in the drawing. FIG. 5(*b*) shows results of the calculation. The intensity profile with x of 0 nm (shown by open circles) corresponds to an ideal light collection profile. The intensity profile with x of 2 nm is plotted by rhombuses, the intensity profile with x of 5 nm by squares, the intensity profile with x of 10 nm by triangles.

It is understood from the foregoing results that the intensity profile with x of 2 nm has small and allowable deviations from the ideal light collection profile, but the intensity profile with x of 5 nm has too large deviations from the ideal light collection profile. Therefore, the knife edge needs to be produced such that the inclination angle of the leading end surface becomes 1 mrad or less. In addition, even if the leading end portion of the knife edge is accurately produced so as to be rectangular in cross section, when the leading end surface of the knife edge held by the moving stage 7 inclines with respect to the optical axis of the X-ray beam, the intensity of the diffraction X-ray also deviates from the ideal light collection profile. Accordingly, it is necessary to set an angle formed by the leading end surface of the knife edge and the optical axis of the X-ray beam at 1 mrad or less as described above. Therefore, the moving stage 7 is structured so as to allow the posture of the knife edge 4 to be arbitrarily fine-tuned.

The oblique incident light collection optical system with an oval X-ray collection mirror has a deep focal depth, and thus realizes measurement with higher spatial resolutions even if a significantly thicker knife edge is used as compared with a full width at half maximum of an X-ray beam. That is, even if an X-ray beam is collected such that a beam waist becomes about 10 nm, it is possible to use a 2,000 nm-thick knife edge rectangular in the shape of a leading edge portion to measure an X-ray intensity profile accurately with nm-order spatial resolutions.

Considering the foregoing results together, the present invention is designed to set the thickness of the knife edge such that a transmission rate of an X-ray passing through the knife edge falls within a range of 80 to 20% and the phase shift of the X-ray becomes 0.3 to 0.7λ(λ denotes a wavelength of the X-ray), and measure by the X-ray detector an X-ray formed by overlapping of a diffracted X-ray that has diffracted at the leading end of the knife edge and come around behind the knife edge and a transmission X-ray that has passed through the knife edge and advanced in phase. Preferably, the thickness of the knife edge is set such that a transmission rate of an X-ray passing through the knife edge falls within a range of 80 to 20% and the phase shift of the X-ray becomes 0.4 to 0.6λ.

Figure 6:
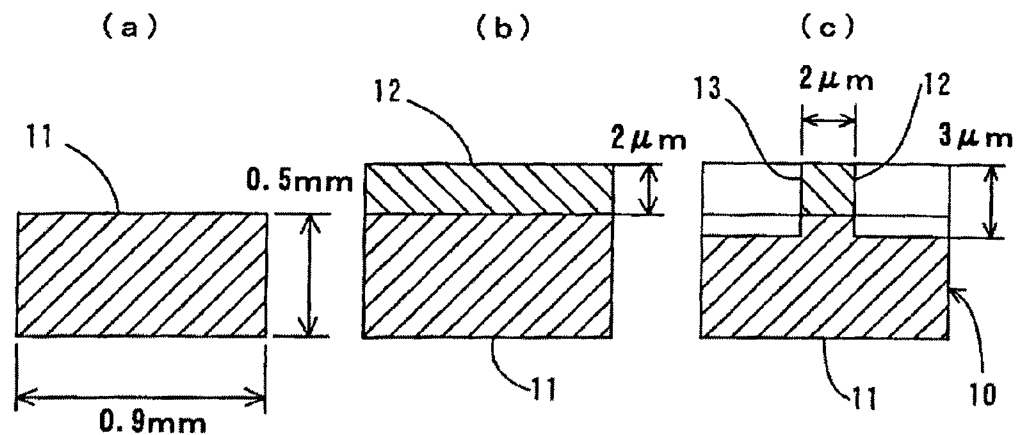
FIG. 6 show a method for manufacturing the knife edge in the present invention.
Figure 7:
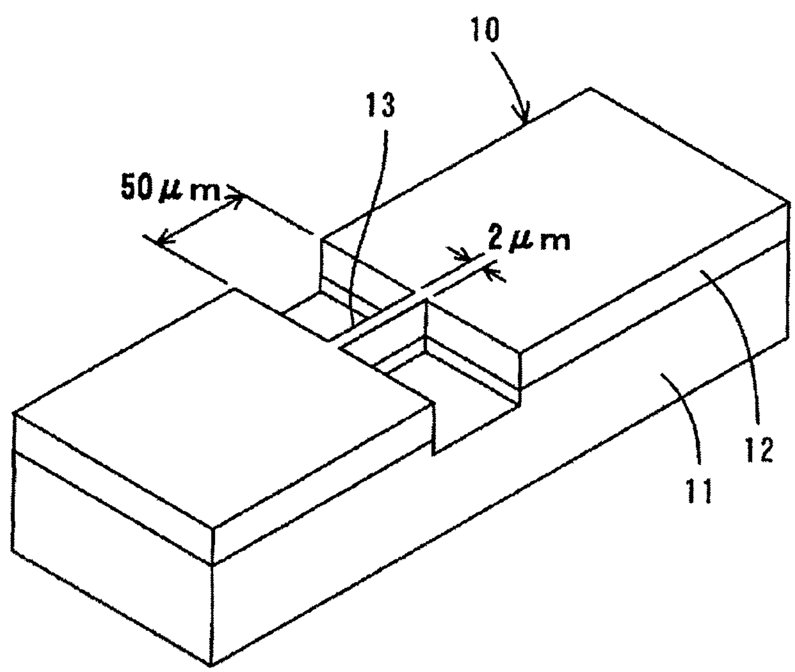
FIG. 7 is a perpendicular view of an outer appearance of an edge member with the knife edge used in the present invention.

Next, a method for manufacturing the knife edge will be described below with reference to FIG. 6. From the foregoing simulation results, the knife edge is to be made of Pt with a thickness of 2,000 nm, a height of 0.5 μm or more, and a width of 50 p.m. First, an Si wafer is cut into a rectangle 0.9×9 mm (0.5 mm thick) to prepare a base 11 (see FIG. 6(*a*)). Next, Pt is evaporated by electron beams on a surface of the base 11 to form a Pt layer 12 with a thickness of 2 μm (see FIG. 6(*b*)), and finally a knife edge 13 with a thickness of 2 μm is carved out by FIB processing (see FIG. 6(*c*)). FIG. 7 shows schematically an entire shape of the edge member 10 with the knife edge 13 formed. In actuality, the base 11 of the edge member 10 is attached to the moving stage 7.

Figure 8:
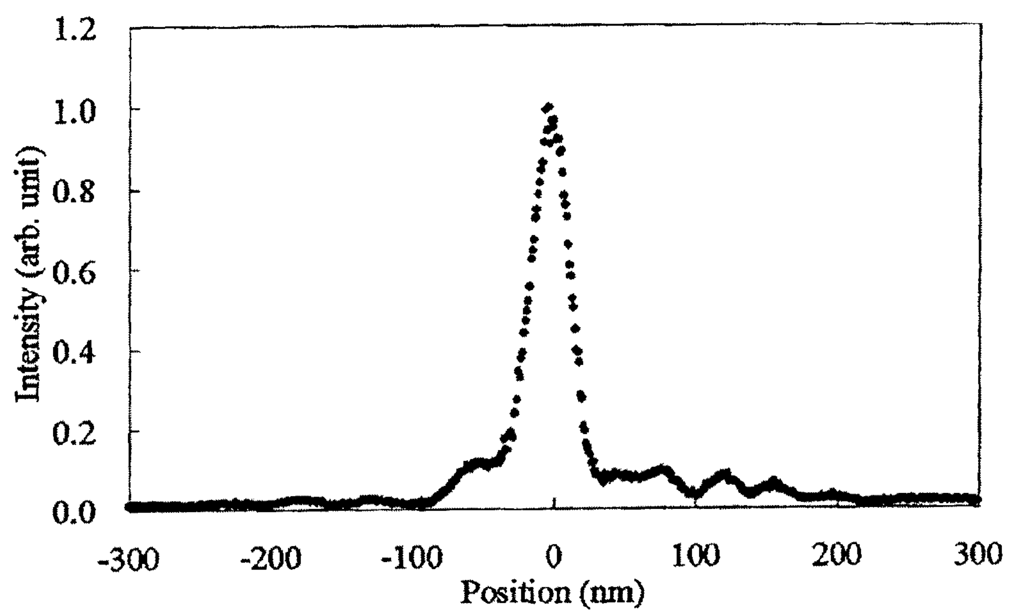
FIG. 8 is a graph of an X-ray beam intensity distribution measured by the present invention.
Figure 15:
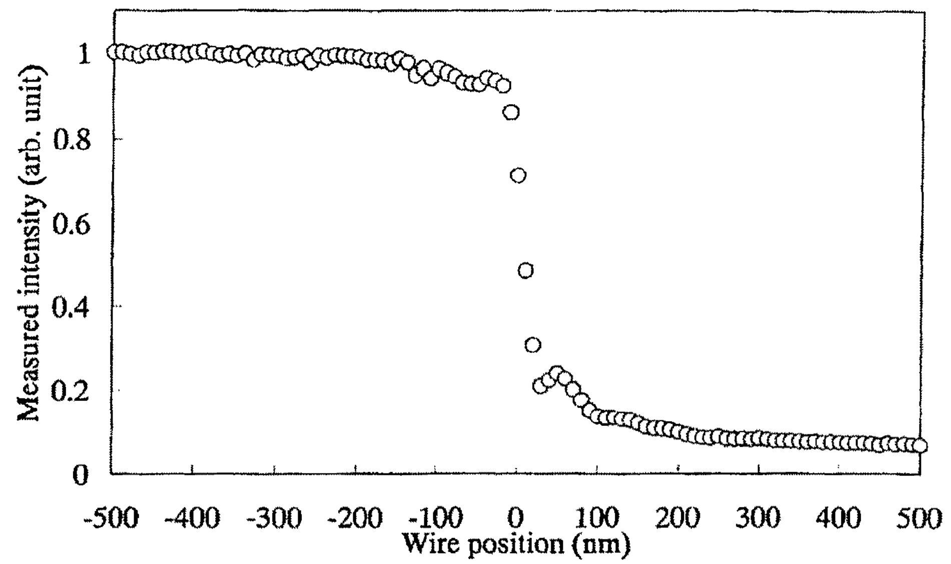
FIG. 15 show results of measurement by the conventional wire scanning method.
Figure 15:
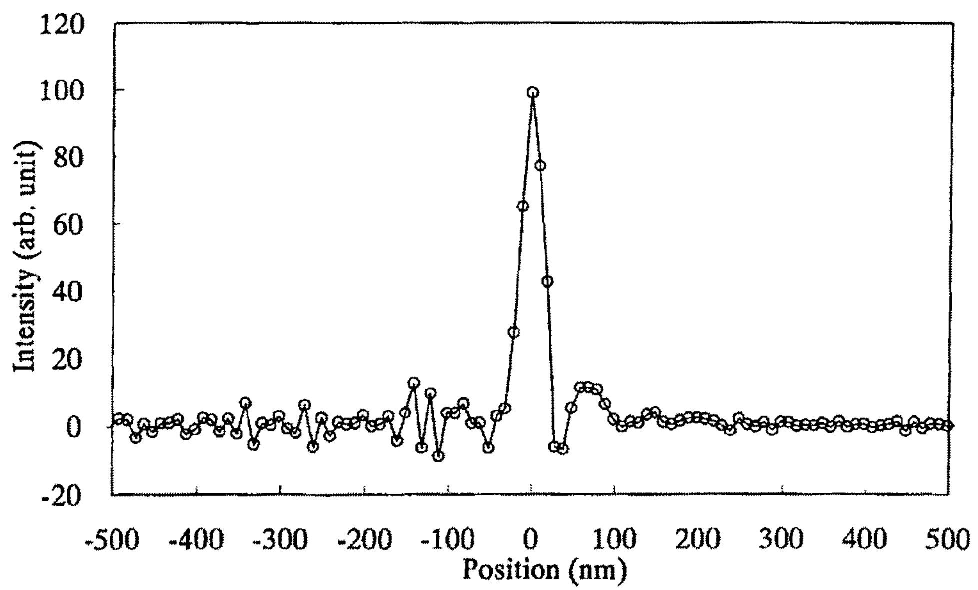

The inventors have used the knife edge as specified above in the measurement optical system of FIG. 1 to measure an X-ray intensity profile of the X-ray beam in the ideal light collection profile of FIG. 3(*b*) on the focal plane. FIG. 8 shows results of the measurement. It is understood from the results that a full width at half maximum of beam waist of the X-ray beam has become slightly larger than 25 nm in the ideal light collection profile, but wave properties have been reproduced in a broad base region. Accordingly, the measurement method in the present invention obviously holds superiority, as compared with the results of measurement by the conventional wire scanning method shown in FIG. 15(*b*).

Figure 9:
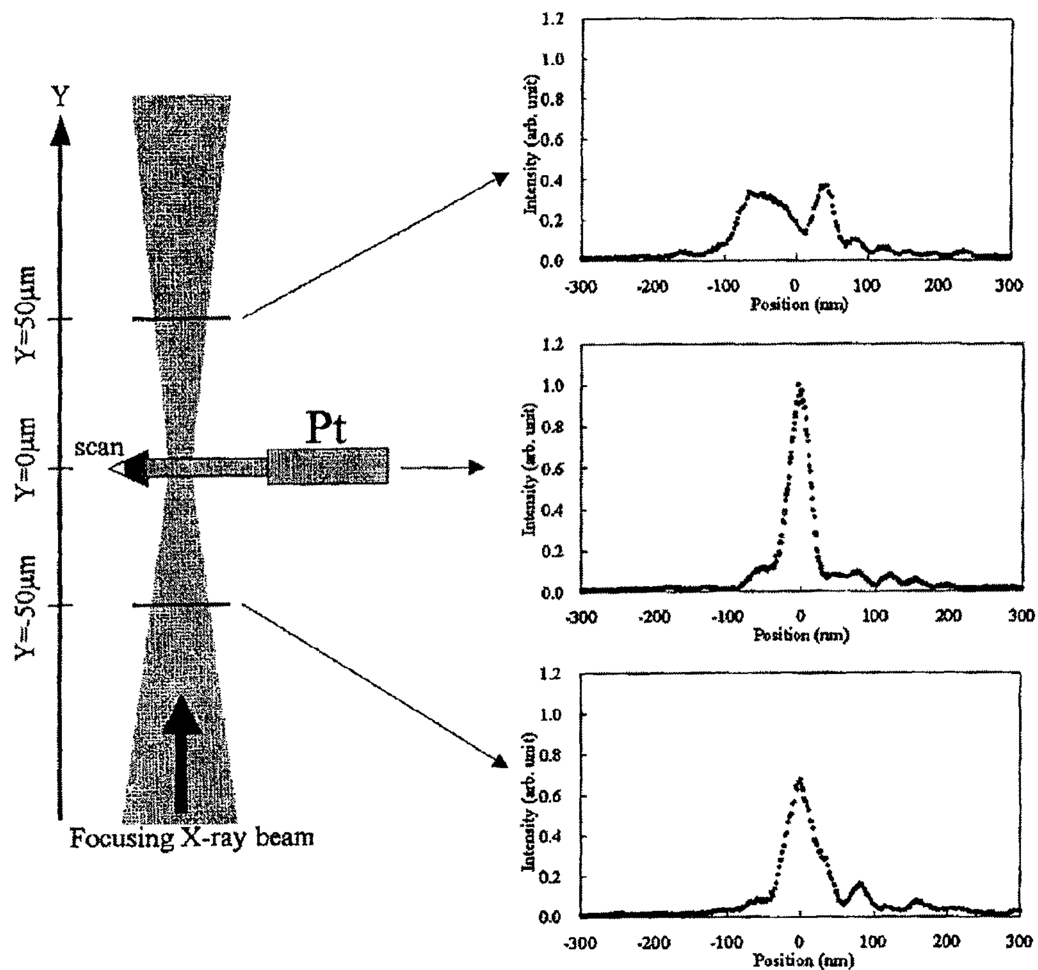
FIG. 9 is graphs of X-ray beam intensity distributions measured on a focal plane and at front and back sides of the same.

FIG. 9 is graphs of X-ray beam intensity distributions measured on the focal plane (Y=0 μm) and at front and back positions of the same (Y=±50 μm). As in the drawing, the measurement method of the present invention allows precise measurement of an X-ray intensity distribution not only on the focal plane but also at positions distant from the focal plane. This allows not only determination of a spot diameter but also analysis of a fine structure of a beam waist, thereby resulting in improvement in quality of light collection. In addition, the present invention also makes it possible to measure X-ray intensity profiles by running the knife edge across an X-ray beam from a plurality of directions and combine the measurements into a three-dimensional intensity profile.

An X-ray may be distorted in wavefront at reflection on an X-ray mirror under influence of shape error of the X-ray mirror and thickness error of a multilayer film on the X-ray mirror. Such influence affects differently an intensity profile of an X-ray beam actually measured on the focal plane, depending on magnitude of the shape error and space wavelength. In such cases, the distorted light collection profile is considered to include information on the shape error of the X-ray mirror. Therefore, the phase error of the X-ray mirror can be calculated by a phase retrieval method from the X-ray intensity profile on the focal plane or in the vicinity of the same (see JP 2006-357566 A). Since the influence of the shape error of the X-ray mirror appears in a broad base region of the X-ray intensity profile of the X-ray beam measured on the focal plane or in the vicinity of the same, it is important to measure precisely an X-ray intensity profile covering a broad base region for accurate calculation of a shape error of the X-ray mirror.

Figure 10:
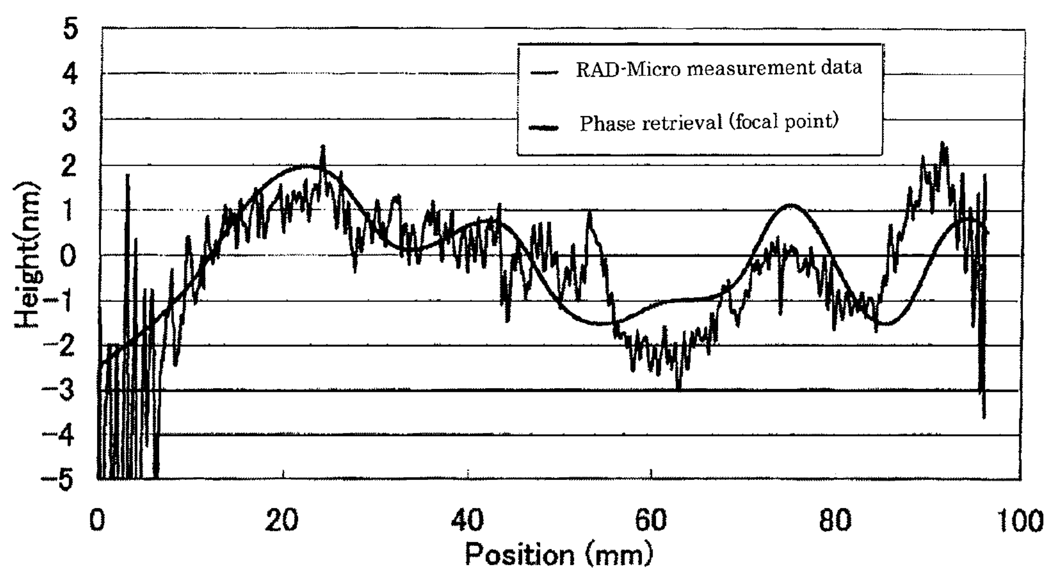
FIG. 10 is a graph showing a shape error distribution of an X-ray mirror calculated by a phase retrieval method only from the X-ray intensity distribution of FIG. 8 and a shape error distribution obtained by off-line measurement (RADSI) using an interferometer.

The inventors have calculated a shape error of the X-ray mirror by the phase retrieval method using the measurement results of the intensity profile of the X-ray beam shown in FIG. 8. FIG. 10 shows calculation results by a bold solid line (in low cycles). FIG. 10 also provides results of off-line measurement using an interferometer by a narrow solid line (in high cycles). The two results exhibit an extremely favorable concordance, which proves high effectiveness and reliability of the measurement method of the present invention. However, even if the thickness of the knife edge is set at a theoretically optimum value, optimum measurement may not be obtained depending on the focal depth of an X-ray beam and other conditions of a measurement apparatus.

Figure 11:
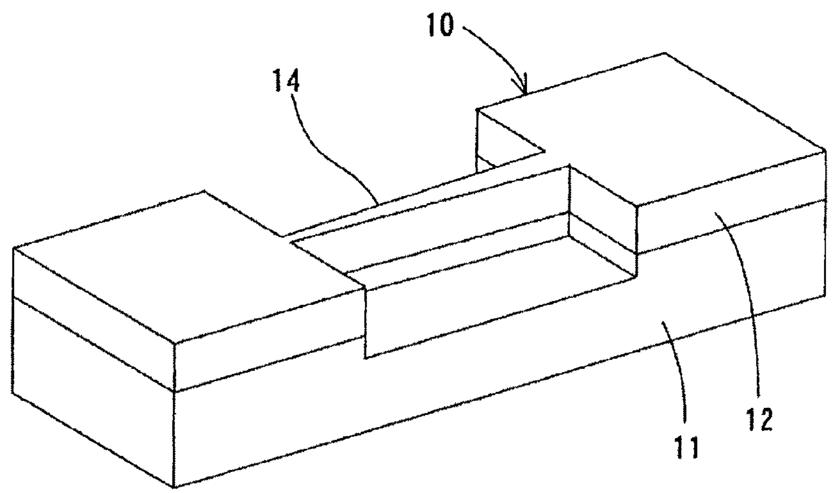
FIG. 11 show the edge member with the knife edge used in the present invention.
Figure 11:
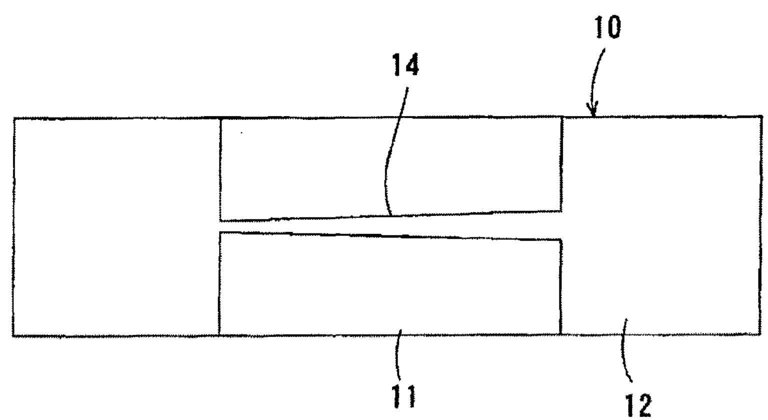
Figure 12:
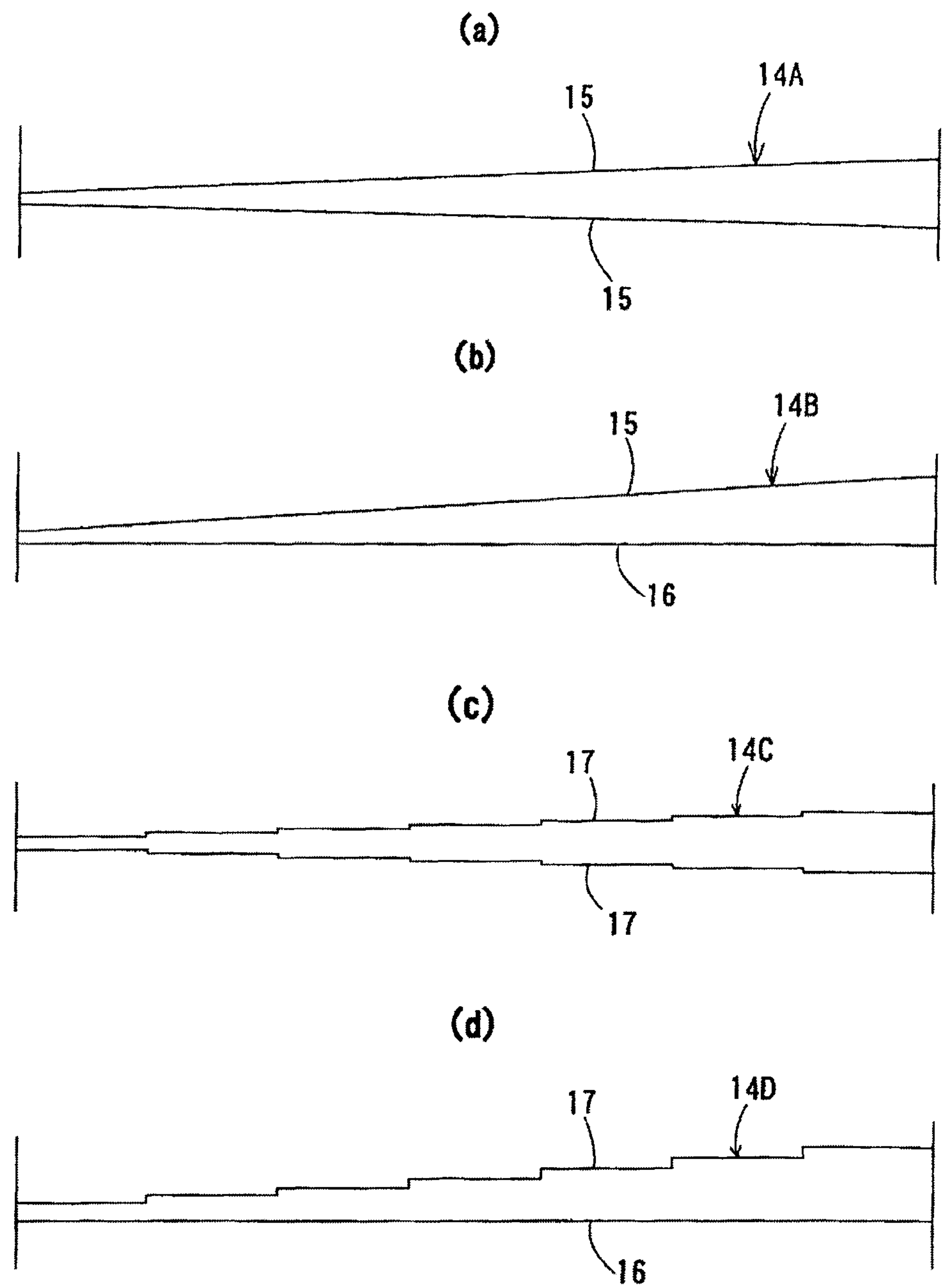
FIG. 12 show embodiments of the knife edge.
Figure 13:
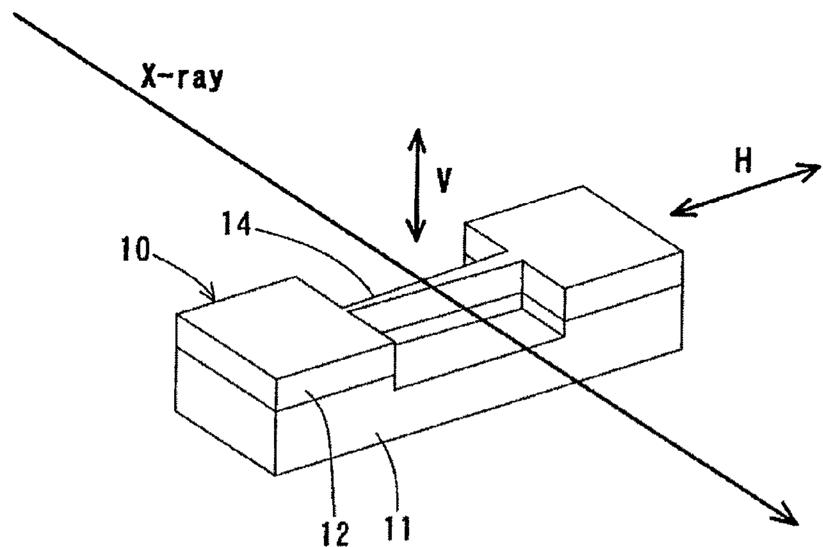
FIG. 13 is a simplified perpendicular diagram showing a relationship between an optical axis of an X-ray and a running direction of the edge member.
Figure 14:
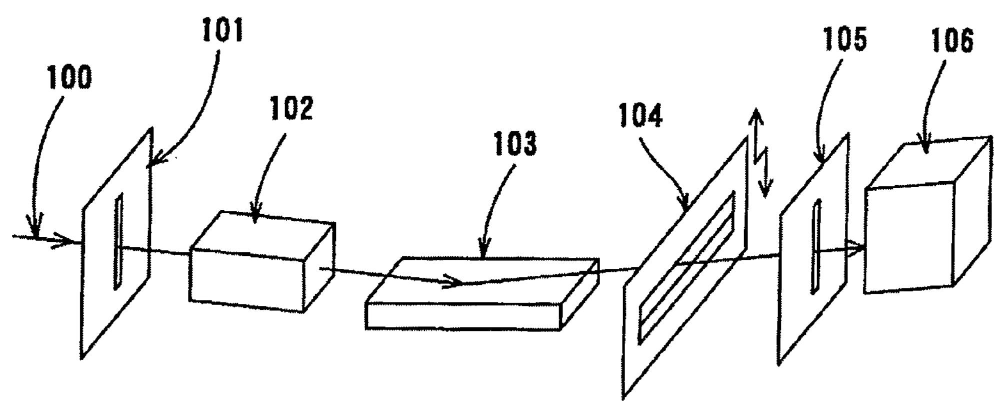
FIG. 14 is a general arrangement diagram of a measurement optical system using a conventional wire scanning method.

Accordingly, the inventors propose a method and apparatus for precise measurement of an X-ray nanobeam intensity distribution using a knife edge varied in thickness continuously or stepwise in a longitudinal direction, as shown in FIGS. 11 to 13. The edge member 10 used in this embodiment has a knife edge 14 formed so as to vary in thickness continuously in a longitudinal direction, as shown in FIG. 11. The knife edge 14 is configured to have a length of 200 μm, a minimum thickness of 1 μm, and a maximum thickness of 5 μm and vary in thickness linearly between the minimum and maximum portions. In this arrangement, if the length of the knife edge 14 is about 200 μm and a diameter of an X-ray beam (FWHM) is 100 nm or less, the thickness of the knife edge 14 can be regarded as approximately constant within the range of the beam diameter, and does not arise any problem in measurement of an X-ray intensity profile. In addition, if the minimum thickness of the knife edge 14 is thinner than 1 μm, the knife edge 14 cannot provide a sufficient amount of phase shift and cannot be readily handled due to its weakened mechanical strength. Meanwhile, if the maximum thickness of the knife edge 14 is larger than 5 μm, transmission attenuation of an X-ray becomes too large to utilize the measurement principle of the present invention using a transmission X-ray, thereby resulting in a deteriorated S/N ratio.

FIG. 12 illustrates various shapes of knife edges 14A, 14B, 14C, and 14D with thickness varied in a longitudinal direction. The knife edge 14A shown in FIG. 12(*a*) is identical to that shown in FIG. 11, but is a tapered two-sided inclination type in which inclined surfaces 15, 15 are formed on both sides so as to be symmetric with respect to a center line, and is continuously changed in thickness in a longitudinal direction. In this arrangement, the inclined surfaces 15 incline with respect to a flat plane orthogonal to the optical axis of an X-ray. The knife edge 14B shown in FIG. 12(*b*) is a single-sided inclination type in which the inclined surface 15 is formed on one side and an orthogonal surface 16 is formed on the other side, and is continuously changed in thickness in a longitudinal direction. In this arrangement, the orthogonal surface 16 refers to a flat plane orthogonal to the optical axis of an X-ray. The knife edge 14C shown in FIG. 12(*c*) is a two-sided stepped type in which stepped surfaces 17, 17 are formed on both sides so as to be symmetric with respect to a center line, and is changed stepwise in thickness in a longitudinal direction. The knife edge 14D shown in FIG. 12(*d*) is a single-sided stepped type in which the stepped surface 17 is formed on one side and the orthogonal surface 16 is formed on the other side, and is changed stepwise in thickness in a longitudinal direction. In any of the foregoing types, the thickness of the knife edge 14 is varied from 1 to 5 μm. In the stepped types, the stepped surfaces 17 are each configured by a flat plane orthogonal to the optical axis of an X-ray. Alternatively, the knife edge 14 may be configured so as to be the thinnest in a middle portion and be made thicker on the both sides thereof in a symmetrical manner.

Then, the edge member 10 with the knife edge 14 formed so as to vary in thickness continuously or stepwise in a longitudinal direction, is fixed to the moving stage 7. As shown in FIG. 13, the moving stage 7 is configured to run the knife edge 14 with nm-order accuracy in two directions orthogonal to the optical axis of an X-ray (V and H directions). In this arrangement, the V direction corresponds to a vertical direction with the base 11 of the edge member 10 horizontally disposed, along the width of the knife edge 14. The H direction corresponds to a horizontal direction with the base 11 of the edge member 10 horizontally disposed, along the length of the knife edge 14. For measurement of an X-ray intensity profile, first, if the wavelength of an X-ray is known, the edge member 10 is run in the H direction to set the knife edge 14 so as to cut across an X-ray beam at a portion with a thickness of a theoretically optimum value. In this arrangement, since the thickness of the knife edge 14 corresponds one-on-one to a coordinate in the H direction, the thickness of the knife edge 14 can be properly set by monitoring the coordinate in the H direction. Then, the edge member 10 is run in the V direction such that the knife edge 14 cuts across the X-ray beam as described above, thereby measuring an X-ray intensity profile.

In addition, an X-ray intensity profile can be measured at maximum sensitivity in such a manner as to: run the edge member 10 in the H direction when part of an X-ray beam contacts the leading end portion of the knife edge 14; measure a diffraction X-ray intensity with respect to the thickness of the knife edge 14 to obtain the thickness-intensity measurement characteristics M as shown in FIG. 4(*b*); specify the thickness of the knife edge 14 with maximum intensity of the X-ray beam; and run the edge member 10 in the H direction to a position with the specified thickness of the knife edge 14, and then run the edge member 10 in the V direction at the position with the specified thickness of the knife edge 14. Even if the wavelength of an X-ray is unknown, a wavelength range of the unknown X-ray can be determined by inverse calculation from comparison between the thickness-intensity measurement characteristics M and thickness-intensity calculation characteristics S obtained by calculating a diffraction X-ray intensity with respect to the wavelength of the X-ray and the thickness of the knife edge. In addition, it is possible to store table data of the thickness-intensity calculation characteristics S with respect to wavelengths of a large number of X-rays in advance in a memory of an X-ray measurement apparatus, thereby to perform promptly data processing at the running in the H direction, which is suitable for measurement of an X-ray intensity profile in real time.

REFERENCE SIGNS LIST

1. Incident X-ray
2. Slit
3. X-ray mirror
4. Knife edge
5. Slit
6. X-ray detector
7. Moving stage
8. Ion chamber
10 Edge member
11. Base
12 Pt layer
13 Knife edge
14, 14A, 14B, 14C, and 14D Knife edge
100 Incident X-ray
101 Slit
102 Ion chamber
103 X-ray mirror
104 Au wire
105 Slit
106 X-ray detector

The invention claimed is:

1. A method for precise measurement of an X-ray nanobeam intensity distribution, comprising the steps of:

using a dark-field metrology to run a knife edge, the knife edge being made of a heavy metal, so as to cut across an X-ray beam and measure an X-ray intensity by an X-ray detector disposed behind the knife edge at a position geometrically dark with respect to an X-ray source;

measuring an X-ray intensity distribution in a cross section of the X-ray beam;

advancing a phase of an X-ray passing through the knife edge, prepared so as to change in thickness continuously or stepwise in a longitudinal direction, and set so as to cut across an X-ray beam at a position of a thickness as to obtain a phase shift with which a transmission X-ray and a diffraction X-ray diffracted by a leading end of the knife edge reinforce each other; and measuring with the X-ray detector an X-ray foamed by overlapping of the diffraction X-ray and the transmission X-ray.

2. The method for precise measurement of an X-ray nanobeam intensity distribution according to claim 1, wherein the knife edge is formed so as to change in thickness from 1 μm to 5 μm continuously or stepwise in a longitudinal direction and is set so as to cut across an X-ray beam at a position of a thickness where a transmission rate of an X-ray passing through the knife edge falls within a range from 80% to 20% and a phase shift becomes 0.3λ to 0.7λ (λ denotes wavelength of an X-ray), and an X-ray formed by overlapping of a diffraction X-ray that has been diffracted at a leading end of the knife edge and come around behind the knife edge and a transmission X-ray that has been passed through the knife edge and advanced in phase, is measured by the X-ray detector.

3. The method for precise measurement of an X-ray nanobeam intensity distribution according to claim 1 or 2, wherein the material for the knife edge is Pt or Au.

4. The method for precise measurement of an X-ray nanobeam intensity distribution according to claim 1 or 2, wherein a leading end portion of the knife edge is rectangular in cross section, and a leading end surface of the knife edge has an inclination angle of 1 mrad or less.

5. The method for precise measurement of an X-ray nanobeam intensity distribution according to claim 1 or 2, wherein the leading end portion of the knife edge is rectangular in cross section, and an angle formed by the leading end surface of the knife edge and an optical axis of an X-ray beam is set at 1 mrad or less.

6. The method for precise measurement of an X-ray nanobeam intensity distribution according to claim 1 or 2, wherein an edge member with the knife edge is run in a direction that the knife edge cuts across an X-ray beam and in a direction along a longer side of the knife edge.

7. An apparatus for precise measurement of an X-ray nanobeam intensity distribution, comprising: an edge member that varies in thickness continuously or stepwise in a longitudinal direction and includes a knife edge with a leading end portion rectangular in cross section and disposed such that an inclination angle of a leading end surface becomes 1 mrad or less with respect to an optical axis of an X-ray beam; a high-accurate moving stage that holds the edge member such that the knife edge is run in a direction that cuts across the X-ray beam and in a direction along a longer side of the knife edge; and an X-ray detector that is disposed behind the knife edge at a position geometrically dark with respect to an X-ray source, wherein the knife edge is made of a heavy metal with the effect of advancing a phase of an X-ray passing through the knife edge and is set so as to cut across an X-ray beam at a position of a thickness as to obtain a phase shift with which a transmission X-ray and a diffraction X-ray diffracted by a leading end of the knife edge reinforce each other, and an X-ray formed by overlapping of the diffraction X-ray and the transmission X-ray is measured by the X-ray detector.

8. The apparatus for precise measurement of an X-ray nanobeam intensity distribution according to claim 7, wherein the knife edge is formed so as to change in thickness from 1 μm to 5 μcontinuously or stepwise in a longitudinal direction and is set so as to cut across an X-ray beam at a position of a thickness where a transmission rate of an X-ray passing through the knife edge falls within a range from 80% to 20% and a phase shift becomes 0.3λ to 0.7λ (λ denotes wavelength of an X-ray), and an X-ray formed by overlapping of a diffraction X-ray that has been diffracted at a leading end of the knife edge and come around behind the knife edge and a transmission X-ray that has been passed through the knife edge and advanced in phase, is measured by the X-ray detector.

9. The apparatus for precise measurement of an X-ray nanobeam intensity distribution according to claim 7 or 8, wherein a slit is arranged in front of the X-ray detector such that an opening thereof is situated at a position geometrically dark with respect to an X-ray source.

* * * * *